United States Patent
Toda et al.

(10) Patent No.: US 10,022,279 B2
(45) Date of Patent: Jul. 17, 2018

(54) DISPOSABLE URINE-ABSORPTION PAD WITH BEDSORE-INHIBITION FUNCTION

(71) Applicant: UNICHARM CORPORATION, Ehime (JP)

(72) Inventors: Haruki Toda, Kagawa (JP); Takahito Nagai, Kagawa (JP)

(73) Assignee: Unicharm Corporation, Ehime (JP)

( * ) Notice: Subject to any disclaimer, the term of this patent is extended or adjusted under 35 U.S.C. 154(b) by 392 days.

(21) Appl. No.: 14/766,082

(22) PCT Filed: Jan. 15, 2014

(86) PCT No.: PCT/JP2014/050598
§ 371 (c)(1),
(2) Date: Aug. 5, 2015

(87) PCT Pub. No.: WO2014/125858
PCT Pub. Date: Aug. 21, 2014

(65) Prior Publication Data
US 2015/0366725 A1  Dec. 24, 2015

(30) Foreign Application Priority Data

Feb. 15, 2013 (JP) ................. 2013-028193

(51) Int. Cl.
*A61F 13/494* (2006.01)
*A61F 13/513* (2006.01)
(Continued)

(52) U.S. Cl.
CPC ...... *A61F 13/513* (2013.01); *A61F 13/47272* (2013.01); *A61F 13/49001* (2013.01);
(Continued)

(58) Field of Classification Search
CPC ............ A61F 13/49413; A61F 13/4942; A61F 13/49466; A61F 13/49473; A61F 13/495;
(Continued)

(56) References Cited

U.S. PATENT DOCUMENTS 4,938,755 A * 7/1990 Foreman ............... A61F 5/4401
604/385.27
5,558,660 A * 9/1996 Dreier ............... A61F 13/49413
604/378

(Continued)

FOREIGN PATENT DOCUMENTS

| CN | 1266672 A | 9/2000 |
|---|---|---|
| CN | 1897900 A | 1/2007 |

(Continued)

OTHER PUBLICATIONS

International Search Report from corresponding PCT application No. PCT/JP2014/050598 dated Apr. 1, 2014 (2 pgs).

*Primary Examiner* — Lynne Anderson
(74) *Attorney, Agent, or Firm* — Brinks Gilson & Lione

(57) ABSTRACT

Provided is a disposable urine-absorption pad with which production costs are reduced, and with which a function for inhibiting the occurrence or aggravation of bedsores is imparted by facilitating relative movement of a skin-contact sheet in a back-and-forth direction with respect to a pad main body. This urine-absorption pad includes: an outer surface sheet; an absorption body; an inner surface sheet; a left side sheet; a right side sheet; an overlap sheet; and a low friction member. The overlap sheet is provided to a gluteal region. A right side edge of the overlap sheet is joined to a left side part of the right side sheet. A left side edge of the overlap sheet is joined to a right side part of the left side sheet. The low friction member is provided between the overlap sheet and the inner surface sheet.

18 Claims, 9 Drawing Sheets

(51) Int. Cl.
*A61F 13/472* (2006.01)
*A61F 13/49* (2006.01)
*A61F 13/511* (2006.01)
*A61F 13/15* (2006.01)
*A61F 13/495* (2006.01)
*A61F 13/496* (2006.01)

(52) U.S. Cl.
CPC ......... *A61F 13/5116* (2013.01); *A61F 13/496* (2013.01); *A61F 13/49473* (2013.01); *A61F 2013/15024* (2013.01); *A61F 2013/15146* (2013.01); *A61F 2013/4956* (2013.01); *A61F 2013/49493* (2013.01); *A61F 2013/51316* (2013.01); *A61F 2013/51322* (2013.01)

(58) Field of Classification Search
CPC .. A61F 2013/15024; A61F 2013/15154; A61F 2013/49053; A61F 2013/49493; A61F 2013/4955; A61F 2013/4956; A61F 2013/51316
See application file for complete search history.

(56) References Cited

U.S. PATENT DOCUMENTS

| | | | |
|---|---|---|---|
| 6,280,426 B1* | 8/2001 | Turner | A61F 13/49466 604/385.01 |
| 6,402,729 B1* | 6/2002 | Boberg | A61F 13/4753 604/385.24 |
| 6,450,996 B1* | 9/2002 | Otsubo | A61F 13/505 604/364 |
| 7,666,173 B2* | 2/2010 | Mishima | A61F 13/4915 604/385.101 |
| 2007/0043330 A1 | 2/2007 | Lankhof et al. | |
| 2012/0311770 A1 | 12/2012 | Nakajima et al. | |

FOREIGN PATENT DOCUMENTS

| | | |
|---|---|---|
| CN | 102844007 A | 12/2012 |
| EP | 1 034 761 A2 | 9/2000 |
| JP | 2007-515218 A | 6/2007 |
| JP | 2008-86494 A | 4/2008 |
| JP | 2011-167412 A | 9/2011 |
| WO | WO 2005/063158 A1 | 7/2005 |

* cited by examiner

DISPOSABLE URINE-ABSORPTION PAD WITH BEDSORE-INHIBITION FUNCTION

RELATED APPLICATION

This application is a 35 U.S.C. § 371 national phase filing of International Patent Application No. PCT/JP2014/050598, filed Jan. 15, 2014, through which and to which priority is claimed under 35 U.S.C. § 119 to Japanese Patent Application No. 2013-028193, filed Feb. 15, 2013, the complete disclosure of which is hereby expressly incorporated by reference.

TECHNICAL FIELD

The present invention relates to a disposable urine-absorption pad with a bedsore-inhibition function. More specifically, the invention relates to a disposable urine-absorption pad with a bedsore-inhibition function to be used together with a tape-type or pants-type diaper cover.

BACKGROUND ART

Disposable urine-absorption pads are known that are to be used together with adult diaper covers, and in the case of bedridden elderly, in particular, the sacrum that juts out from other sections when sleeping face-up is pressed against the bed by its own weight, potentially causing bedsores. Attempts have therefore been made to provide disposable urine-absorption pads with a function that prevents occurrence or aggravation of bedsores.

For example, JP 2011-167412 A discloses a disposable urine-absorption pad comprising a skin-contact sheet on a urine-absorption pad main body, and further imparted with a function of preventing creation and aggravation of bedsores by formation of friction resistance-reducing means between the skin-contact sheet and the urine-absorption pad main body.

CITATION LIST

Patent Document

[Patent document 1] Japanese Unexamined Patent Publication No. 2011-167412

DISCLOSURE OF THE INVENTION

Problems to be Solved by the Invention

However, the disposable urine-absorption pad of JP 2011-167412 A has both edges of the skin-contact sheet bonded to the pad main body, and when the disposable urine-absorption pad has a barrier cuff, the skin-contact sheet becomes attached between the barrier cuff and the pad main body. Or alternatively, even when the skin-contact sheet is bonded to the barrier cuff, the front and rear ends of the barrier cuff become anchored to the pad main body.

When the skin-contact sheet is directly bonded to the pad main body, the dimensions of the skin-contact sheet are larger than when the skin-contact sheet is bonded to the barrier cuff, and therefore the amount of material in the skin-contact sheet is greater, thus increasing production cost. From the viewpoint of production cost, therefore, the skin-contact sheet is preferably bonded to the barrier cuff.

When the skin-contact sheet is bonded to the barrier cuff, since the front and rear ends of the barrier cuff of JP 2011-167412 A are anchored to the pad main body, relative movement of the skin-contact sheet in the longitudinal direction with respect to the pad main body is inhibited. In the case of bedridden elderly, however, when the bed is elevated to raise the upper body, the gluteal region is shifted forward by the weight of the body, and even for an elderly person using a wheelchair, the gluteal region is gradually shifted forward by the weight of the body during use of the wheelchair, and this can lead to occurrence or aggravation of bedsores. Thus, when the gluteal region has been shifted forward, it is preferred for the skin-contact sheet to move together with the gluteal region even if the pad main body does not move, or in other words, the skin-contact sheet preferably moves easily in the longitudinal direction relative to the pad main body.

The present invention provides a disposable urine-absorption pad that reduces production cost while having a function of preventing occurrence or aggravation of bedsores, by providing facilitated movement of the skin-contact sheet in the longitudinal direction relative to the pad main body.

Means for Solving the Problems

The present invention is a disposable urine-absorption pad with a bedsore-inhibition function, having front and rear and left and right ends, a body side and clothing side, and an abdominal region, crotch region and gluteal region in that order from front to rear, wherein the pad includes an outer side sheet, an absorbent body provided on the body side of the outer side sheet, an inner side sheet provided on the body side of the absorbent body, a left side sheet provided on the left side section of the pad and a right side sheet provided on the right side section of the pad, the left side edge of the left side sheet matching the left side edge of the outer side sheet, and the left side sheet and the outer side sheet being bonded along the left side edge, and the right side edge of the right side sheet matching the right side edge of the outer side sheet, and the right side sheet and the outer side sheet being bonded along the right side edge, the right side edge of the left side sheet and the left side edge of the right side sheet being straight linear and located more toward the body side than the inner side sheet, and forming free ends without being bonded to the inner side sheet, and an elastic member being provided on at least a portion of the right side edge of the left side sheet and at least a portion of the left side edge of the right side sheet, so that the left side sheet and the right side sheet form barrier cuffs, wherein the pad further includes an overlap sheet and a low friction member, the overlap sheet being provided in the gluteal region, the right side edge of the overlap sheet being bonded to the left side section of the right side sheet, the left side edge of the overlap sheet being bonded to the right side section of the left side sheet, and the low friction member being provided between the overlap sheet and the inner side sheet.

The present invention includes the following embodiments [1] to [20].

[1] A disposable urine-absorption pad with a bedsore-inhibition function, having front and rear and left and right ends, a body side and clothing side, and an abdominal region, crotch region and gluteal region in that order from front to rear, wherein the pad includes an outer side sheet, an absorbent body provided on the body side of the outer side sheet, an inner side sheet provided on the body side of the absorbent body, a left side sheet provided on the left side section of the pad and a right side sheet provided on the right side section of the pad, the left side edge of the left side sheet matching the left side edge of the outer side sheet, and the left side sheet and the outer side sheet being bonded along the left side edge, and the right side edge of the right side sheet matching the right side edge of the outer side sheet, and the right side sheet and the outer side sheet being bonded along the right side edge, the right side edge of the left side sheet and the left side edge of the right side sheet being straight linear and located more toward the body side than the inner side sheet, and forming free ends without being bonded to the inner side sheet, and an elastic member being provided on at least a portion of the right side edge of the left side sheet and at least a portion of the left side edge of the right side sheet, so that the left side sheet and the right side sheet form barrier cuffs, wherein the pad further includes an overlap sheet and a low friction member, the overlap sheet being provided in the gluteal region, the right side edge of the overlap sheet being bonded to the left side section of the right side sheet, the left side edge of the overlap sheet being bonded to the right side section of the left side sheet, and the low friction member being provided between the overlap sheet and the inner side sheet.

[2] A disposable urine-absorption pad with a bedsore-inhibition function according to [1], wherein the rear end of the right side edge of the left side sheet and the rear end of the left side edge of the right side sheet are not bonded to the inner side sheet.

[3] A disposable urine-absorption pad with a bedsore-inhibition function according to [1] or [2], wherein the rear end edge of the overlap sheet matches the rear end edge of the inner side sheet, the rear end edge of the overlap sheet being bonded to the inner side sheet via a tacky section.

[4] A disposable urine-absorption pad with a bedsore-inhibition function according to [3], wherein the tacky section is formed of a different member than the overlap sheet.

[5] A disposable urine-absorption pad with a bedsore-inhibition function according to [3], wherein the tacky section is formed by folding over the overlap sheet.

[6] A disposable urine-absorption pad with a bedsore-inhibition function according to any one of [1] to [5], wherein the overlap sheet is formed of a sheet that can expand and contract in at least one direction.

[7] A disposable urine-absorption pad with a bedsore-inhibition function according to [6], wherein the overlap sheet is disposed so that the direction in which the overlap sheet can expand and contract matches the front-rear direction of the pad.

[8] A disposable urine-absorption pad with a bedsore-inhibition function according to any one of [1] to [7], wherein the overlap sheet is bonded to the surface on the clothing side of the side sheet.

[9] A disposable urine-absorption pad with a bedsore-inhibition function according to any one of [1] to [8], wherein the elastic member is not provided on at least the rear half of the section where the left side edge of the right side sheet and the right side edge of the left side sheet overlap with the overlap sheet.

[10] A disposable urine-absorption pad with a bedsore-inhibition function according to [9], wherein the elastic member provided on the left side edge of the right side sheet and the right side edge of the left side sheet is provided only on the sections where the overlap sheet is not provided.

[11] A disposable urine-absorption pad with a bedsore-inhibition function according to any one of [1] to [10], wherein the overlap sheet is also provided in the abdominal region.

[12] A disposable urine-absorption pad with a bedsore-inhibition function according to any one of [1] to [11], wherein the front end edge of the overlap sheet provided in the gluteal region has a shape that is indented toward the rear.

[13] A disposable urine-absorption pad with a bedsore-inhibition function according to any one of [1] to [12], wherein the rear end edge of the overlap sheet provided in the abdominal region has a shape that is indented toward the front.

[14] A disposable urine-absorption pad with a bedsore-inhibition function according to any one of [1] to [13], wherein the low friction member is provided on the body side surface of the inner side sheet, and in the region contacting with the overlap sheet.

[15] A disposable urine-absorption pad with a bedsore-inhibition function according to any one of [1] to [13], wherein the low friction member is provided on the clothing side surface of the overlap sheet, and in the region contacting with the inner side sheet.

[16] A disposable urine-absorption pad with a bedsore-inhibition function according to any one of [1] to [15], wherein the elastic member is provided on the rear end edge of the overlap sheet.

[17] A disposable urine-absorption pad with a bedsore-inhibition function according to any one of [1] to [16], wherein the low friction member is composed of a low friction sheet with holes.

[18] A disposable urine-absorption pad with a bedsore-inhibition function according to any one of [1] to [17], wherein a plurality of low friction members are disposed at spacings.

[19] A disposable urine-absorption pad with a bedsore-inhibition function according to any one of [1] to [18], wherein the region where the overlap sheet is provided has a region without the absorbent body or a region where the absorbent body has a relatively low basis weight.

[20] A disposable urine-absorption pad with a bedsore-inhibition function according to any one of [1] to [19], wherein the overlap sheet is a hydrophilic sheet.

Effect of the Invention

The disposable urine-absorption pad with a bedsore-inhibition function of the invention can be produced at low cost, and since the overlap sheet easily moves in the longitudinal direction relative to the inner side sheet, it has a function of preventing occurrence or aggravation of bedsores.

BEST MODE FOR CARRYING OUT THE INVENTION

Figure 1:
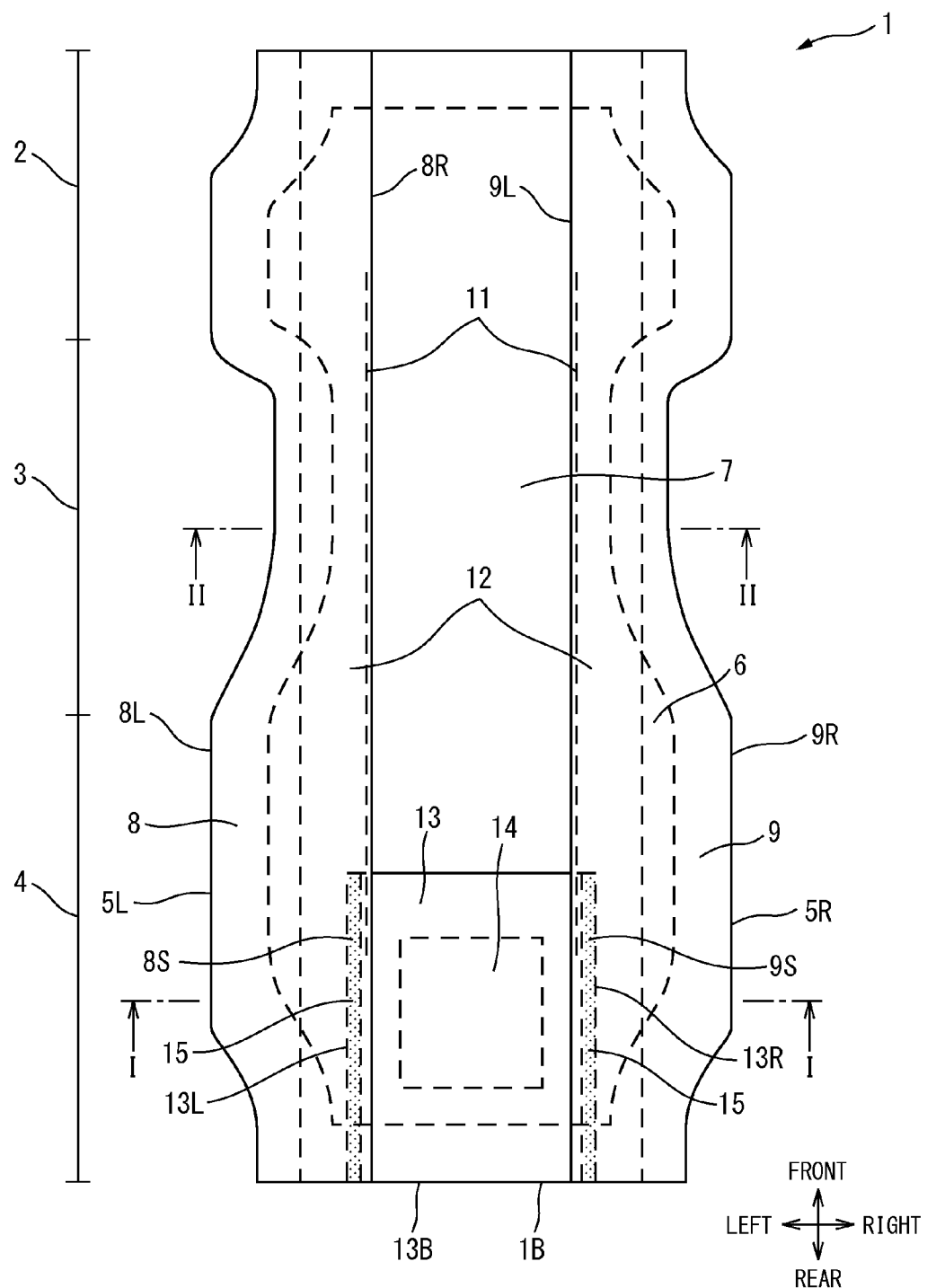
FIG. 1 is a plan view of a disposable urine-absorption pad with a bedsore-inhibition function according to a first embodiment of the invention.

The invention will now be described with reference to the accompanying drawings, with the understanding that the invention is not limited to the examples depicted in the drawings.

Figure 2:
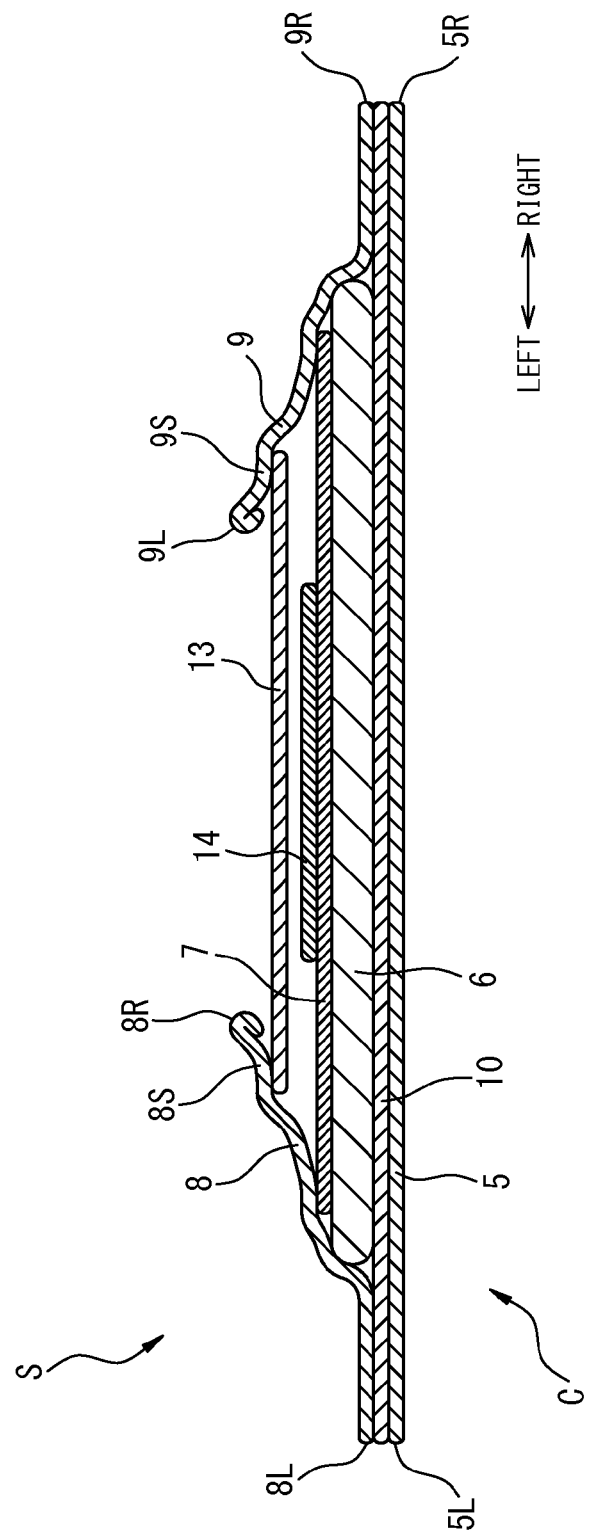
FIG. 2 is a cross-sectional view along line I-I of FIG. 1.
Figure 3:
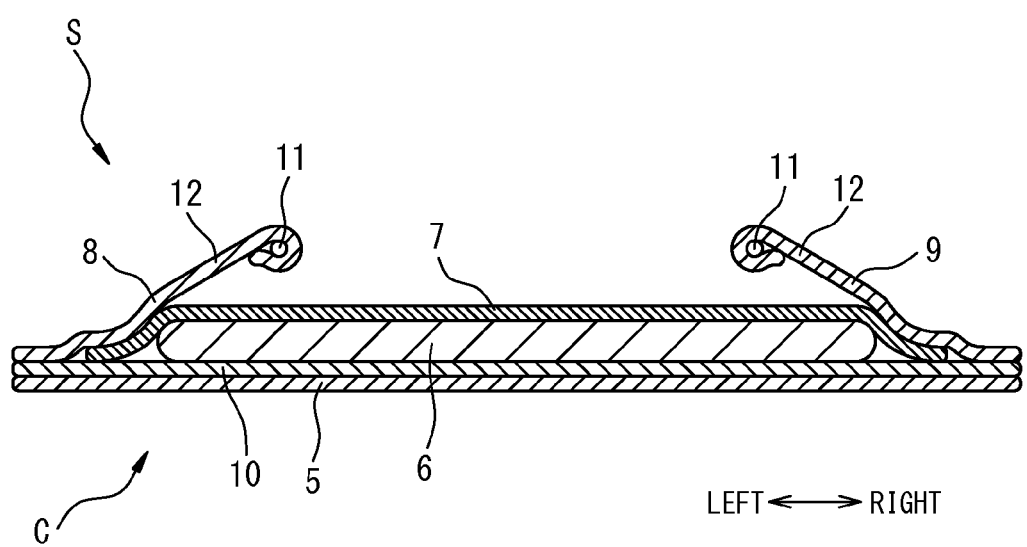
FIG. 3 is a cross-sectional view along line II-II of FIG. 1.

FIG. 1 is a plan view of a first embodiment of a disposable urine-absorption pad with a bedsore-inhibition function of the invention (hereunder also referred to simply as "urine-absorption pad"), FIG. 2 is a cross-sectional view along line I-I of FIG. 1, and FIG. 3 is a cross-sectional view along line II-II of FIG. 1.

The urine-absorption pad 1 has a front and rear and left and right end, a body side S and a clothing side C, and an abdominal region 2, a crotch region 3 and a gluteal region 4 in that order from front to rear.

The urine-absorption pad 1 includes an outer side sheet 5, an absorbent body 6 provided on the body side of the outer side sheet, an inner side sheet 7 provided on the body side of the absorbent body, a left side sheet 8 provided on the left side section of the pad, and a right side sheet 9 provided on the right side section of the pad. For this embodiment, a leak-preventing film 10 is further provided between the outer side sheet 5 and the absorbent body 6. It is not necessarily essential to provide the leak-preventing film 10 if the outer side sheet 5 is liquid-impermeable.

The left side edge 8L of the left side sheet matches the left side edge 5L of the outer side sheet, the left side sheet and outer side sheet being bonded along the left side edge, and the right side edge 9R of the right side sheet matches the right side edge 5R of the outer side sheet, the right side sheet and outer side sheet being bonded along the right side edge.

The right side edge 8R of the left side sheet and the left side edge 9L of the right side sheet are straight linear and are located more toward the body side than the inner side sheet, and form free ends that are not bonded to the inner side sheet, while an elastic member 11 is provided on at least a portion of the right side edge of the left side sheet and at least a portion of the left side edge of the right side sheet, such that the left side sheet and the right side sheet form barrier cuffs 12.

The urine-absorption pad 1 further includes an overlap sheet 13 and a low friction member 14, the overlap sheet 13 being provided in the gluteal region 4, the right side edge 13R of the overlap sheet being bonded to the left side section 9S of the right side sheet, the left side edge 13L of the overlap sheet being bonded to the right side section 8S of the left side sheet, and the low friction member 14 being provided between the overlap sheet 13 and the inner side sheet 7.

Since the low friction member 14 is provided between the overlap sheet 13 and the inner side sheet 7 in the urine-absorption pad of the invention, friction resistance between the overlap sheet 13 and the inner side sheet 7 is low, and the overlap sheet 13 moves relatively easily against the inner side sheet 7.

Also, the right side edge 13R of the overlap sheet is bonded to the left side section 9S of the right side sheet, while the left side edge 13L of the overlap sheet is bonded to the right side section 8S of the left side sheet. In other words, the left and right edges of the overlap sheet are bonded to the barrier cuffs 12. That is, the overlap sheet does not extend to the left and right edges of the urine-absorption pad. Consequently, the overlap sheet of the invention can have reduced dimensions and can reduce starting material costs, compared to when the overlap sheet is bonded at both the right and left edges of the urine-absorption pad.

Furthermore, since the overlap sheet 13 is bonded to the barrier cuff 12 and is not directly anchored to the urine-absorption pad main body ("urine-absorption pad main body" meaning the section comprising the outer side sheet, the absorbent body and the inner side sheet), there is no restriction of movement by the urine-absorption pad main body. Because the overlap sheet is bonded to the barrier cuff which instead has a large degree of freedom of movement, the overlap sheet moves relatively easily against the urine-absorption pad main body.

Furthermore, since the overlap sheet is bonded to the barrier cuff, erection of the barrier cuff when it is worn causes the overlap sheet to rise up from the inner side sheet, thus reducing transfer of excreta onto the body side surface of the overlap sheet.

In FIG. 1, 15 indicates the bonding region between the overlap sheet and the side sheet. The dimensions of the bonding region in the left-right direction are not particularly restricted so long as bonding is of sufficient strength to avoid slippage during wear, but it is preferably 5 to 30 mm, more preferably 10 to 25 mm and even more preferably 15 to 20 mm. The method of bonding the overlap sheet and the side sheet is not particularly restricted, and bonding may be accomplished using an adhesive, heat sealing or the like. The bonding is preferably accomplished with a hot-melt adhesive.

The overlap sheet is provided in the region which is prone to bedsores. That is, it is provided at least in the region that contacts the sacrum of the wearer when the urine-absorption pad is worn. This region is present in the gluteal region 4. The overlap sheet 13 is therefore provided in the gluteal region 4.

Since there will be more room for placement of the sacrum the farther the overlap sheet 13 is to the rear of the urine-absorption pad, the overlap sheet 13 preferably extends to the rear end edge 1B of the urine-absorption pad. Specifically, the rear end edge 13B of the overlap sheet preferably matches the rear end edge 1B of the urine-absorption pad.

So long as the overlap sheet is present at least in the region that contacts with the sacrum of the wearer, the dimension in the longitudinal direction of the overlap sheet is not particularly restricted, but it is preferably 25 to 100%, more preferably 40 to 80% and even more preferably 40 to 70% of the dimension in the longitudinal direction of the gluteal region 4. As will be explained below, when the front end edge of the overlap sheet has a shape that is indented toward the rear, the dimension in the longitudinal direction of the overlap sheet is the shortest dimension in the longitudinal direction of the overlap sheet.

The dimension in the left-right direction of the overlap sheet 13 is not particularly restricted so long as the overlap sheet is present at least in the region that contacts with the sacrum of the wearer. However, because the overlap sheet 13 is anchored at both edges, a larger left-right direction dimension is preferred as it will increase the degree of freedom of movement in the longitudinal direction, and prevent occurrence or aggravation of bedsores. However, in order to increase the dimension in the left-right direction of the overlap sheet 13 the barrier cuff must be situated on the outer side, and this is not preferred from the viewpoint of preventing leakage. It is therefore preferred to balance preventing occurrence or aggravation of bedsores with preventing leakage. For example, the dimension in the left-right direction of the overlap sheet 13 is preferably 70 to 130 cm, more preferably 80 to 120 cm and even more preferably 90 to 110 cm. As will be explained below, when the overlap sheet is bonded to the clothing side surface of the side sheet, the dimension in the left-right direction of the overlap sheet referred to here is the dimension between the right side edge of the left side sheet and the left side edge of the right side sheet (i.e. the "usable dimension").

The material composing the overlap sheet is not particularly restricted, and there may be used a nonwoven fabric, woven fabric, knitted fabric, plastic film or the like, which may be either hydrophilic or hydrophobic. A soft material is preferred, as it will be located in a section of high body pressure. For example, it may be composed of an air-through nonwoven fabric. If it is hydrophobic, it can exhibit an effect of preventing dampening of the gluteal region of the wearer, and therefore a highly water-resistant material is preferred. Conversely, using a hydrophilic material has the effect of allowing excreted sweat to pass through the clothing side, and also has the advantage of allowing urine that has come into contact with the overlap sheet to pass through the overlap sheet and be absorbed by the urine-absorption pad main body.

The overlap sheet is preferably formed of a sheet that can expand and contract in at least one direction. When the overlap sheet is formed of a sheet that can expand and contract, the overlap sheet can move together with the gluteal region when the gluteal region moves, thereby preventing occurrence or aggravation of bedsores. For example, when an overlap sheet formed of a sheet that can expand and contract in one direction is used, if the overlap sheet is oriented so that the direction in which the overlap sheet can expand and contract matches the longitudinal direction of the urine-absorption pad, the overlap sheet will be able to move together with the gluteal region even when the gluteal region has shifted forward upon raising the bed or during use of a wheelchair, thereby helping to prevent occurrence or aggravation of bedsores.

The sheet that can expand and contract in at least one direction is not particularly restricted so long as it is stretchable, and for example, there may be used a nonwoven fabric or a woven or knitted fabric containing elastic fibers, a nonwoven fabric having a surface with alternating ridges and furrows, a gear stretched nonwoven fabric, or a nonwoven fabric or a woven or knitted fabric bearing an elastic member. A nonwoven fabric having a surface with alternating ridges and furrows can be produced, for example, by transporting a fiber web, obtained by passing an aggregate of fibers through a carding machine to open and accumulate the fibers, while spraying a fluid from a plurality of nozzles aligned in the direction perpendicular to the direction of transport, to form furrows at the sections where the fluid has been sprayed. A nonwoven fabric having a surface having alternating ridges and furrows allows stretching in the direction perpendicular to the direction in which the ridges and furrows extend. A nonwoven fabric having a surface with alternating ridges and furrows not only has stretchability but also has minimal contact area with the skin and low irritation to the skin, and is therefore particularly preferred for use as an overlap sheet.

In the urine-absorption pad of the invention, a low friction member 14 is provided between the overlap sheet 13 and the inner side sheet 7. The low friction member 14 may be provided on the body side surface of the inner side sheet 7, or it may be provided on the clothing side surface of the overlap sheet 13. When the low friction member 14 is liquid-impermeable or gas-impermeable, and the low friction member is provided on the surface of the inner side sheet, it can potentially interfere with the liquid permeability or gas permeability of the surface of the inner side sheet, and therefore when the liquid permeability or gas permeability of the inner side sheet is considered important, it is preferred to provide the low friction member on the clothing side surface of the overlap sheet 13. Conversely, when the overlap sheet is stretchable and the low friction member is not stretchable, providing a low friction member on the surface of the overlap sheet can cause the low friction member to potentially interfere with the stretching behavior of the overlap sheet, and therefore when the stretchability of the overlap sheet is considered important, it is preferred to provide the low friction member on the body side surface of the inner side sheet.

The low friction member is not particularly restricted so long as it reduces friction resistance, and for example, there may be used a base sheet coated with a silicone resin. The base sheet used may be a plastic film formed of a thermoplastic resin such as polyethylene or polypropylene, the film being coated with a silicone resin with a mass of approximately 0.6 to 0.8 $g/m^2$. The silicone resin used may be in the form of a solvent system, a solventless system or an emulsion system, and in terms of differences in curing, it may be thermosetting or ultraviolet curing. When a thermoplastic film is used as the base sheet, however, it is preferred to use an ultraviolet curing silicone resin because heating to cure the silicone resin can potentially result in melting of the base sheet.

In addition, the inner side sheet or overlap sheet may be directly coated with a silicone resin, without using a base sheet, at the location where the low friction member is to be provided. In this case, the silicone resin itself constitutes the low friction member. When using a nonwoven fabric as the inner side sheet or overlap sheet, the mass of the silicone resin may be about 1.0 to 1.5 $g/m^2$. The coating method used may be a spray system, roll system, dip system or the like, but considering that coating is on only one side, it is preferred to employ a spray system or roll system.

A fluorine resin may also be used instead of a silicone resin.

The static friction coefficient on the surface of the low friction member 14 is preferably 0.1 to 0.8, more preferably 0.1 to 0.5 and even more preferably 0.1 to 0.3. The dynamic friction coefficient on the surface of the low friction member 14 is preferably 0.1 to 0.75, more preferably 0.1 to 0.45 and even more preferably 0.1 to 0.35.

The static friction coefficient and dynamic friction coefficient may be measured according to JIS P8147 (b), Horizontal plane method. However, the test piece for the horizontal plate was a Union fabric #3 (shirting #3) friction cotton cloth conforming to JIS L0803, and the test piece for the weight was the low friction member 14.

The low friction member 14 may be situated in the same area, or in a wider area, as the region where the overlap sheet is present, but since this increases the amount of starting material usage and does not improve the friction resistance-reducing effect commensurately with the increased cost, and contrarily can also have the adverse effect of interfering with the liquid permeability or gas permeability, it is sufficient to provide it only in a more narrow area than the region in which the overlap sheet is present. When the low friction member is present on the inner side sheet, it is preferred to be one size smaller than the length of the overlap sheet to fit on the inside, so that the low friction member is not exposed even when the overlap sheet has slid. For example, the area of the low friction member 14 may be 10 to 80%, preferably 20 to 60% and more preferably 25 to 40% of the area of the overlap sheet. The location in which the low friction member 14 is disposed is not particularly restricted so long as it is within the region in which the overlap sheet is present, but preferably it is at approximately the center of the region in which the overlap sheet is present.

The base sheet of the low friction member is bonded to the inner side sheet or overlap sheet using commonly known bonding means such as a hot-melt adhesive. The bonding means may be continuous coating, or discontinuous coating, in the longitudinal direction and the left-right direction. Discontinuous coating by coating means can ensure air permeability and prevent mustiness in the urine-absorption pad.

Figure 9:
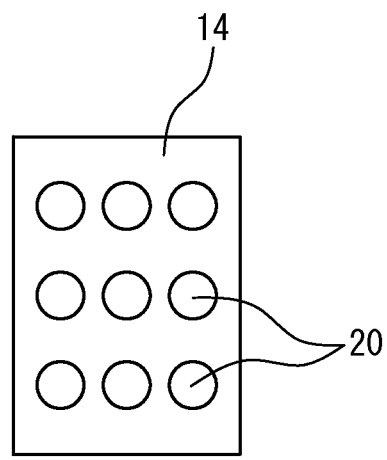
FIG. 9 is a diagram showing an example of a low friction member shape.
Figure 10:
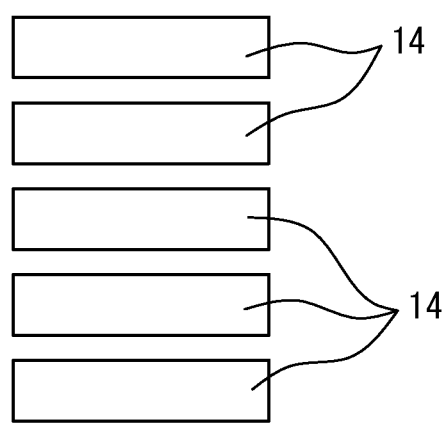
FIG. 10 is a diagram showing another example of a low friction member shape.

There are no particular restrictions on the shape of the low friction member, and it may be any shape that exhibits a friction-reducing effect, such as square, rectangular, circular, elliptical, rhomboid, hexagonal or octagonal. Also, the low friction member may be composed of a sheet having holes 20, as shown in FIG. 9. When a low friction member 14 having holes 20 is provided on the inner side sheet, it is possible to ensure liquid permeability by the holes 20, and to absorb excreta such as urine even when the excreta has come into contact with the low friction member. Also, as shown in FIG. 10, a plurality of low friction members may be disposed with spacings between them. By disposing them with spacings, it is possible to ensure liquid permeability while reducing the amount of starting material usage and lowering production cost.

The left side edge 8L of the left side sheet 8 matches the left side edge 5L of the outer side sheet 5, and the right side edge 9R of the right side sheet 9 matches the right side edge 5R of the outer side sheet 5. The left side sheet 8 and the outer side sheet 5 are bonded along the left side edge, and the right side sheet 9 and the outer side sheet 5 are bonded along the right side edge. However, when a leak-preventing film 10 is provided between the outer side sheet 5 and the absorbent body 6 and the outer side sheet 5 and the leak-preventing film 10 have the same shape and size, the left side sheet 8 may be bonded to the leak-preventing film 10 along the left side edge, and the right side sheet 9 may be bonded to the leak-preventing film 10 along the right side edge. Stated differently, the left side sheet 8 and the outer side sheet 5 may be bonded through the leak-preventing film 10.

The right side edge 8R of the left side sheet 8 and the left side edge 9L of the right side sheet 9 are straight linear and are located more toward the body side than the inner side sheet 7, and form free ends that are not bonded to the inner side sheet 7, while an elastic member 11 is provided on at least a portion of the right side edge 8R of the left side sheet 8 and at least a portion of the left side edge 9L of the right side sheet 9, such that a pair of barrier cuffs 12, 12 are formed. The barrier cuffs prevent leakage of excreta such as urine from the left and right sides.

The elastic member 11 may be provided across the full lengths of the right side edge 8R of the left side sheet 8 and the left side edge 9L of the right side sheet 9, but it does not necessarily have to be provided along the full lengths, nor does the elastic member 11 need to be provided at the section close to the rear end of the urine-absorption pad and the section close to the front end of the urine-absorption pad. In order to avoid warping of the edges of the urine-absorption pad, the elastic member is preferably not provided at the section close to the rear end of the urine-absorption pad and the section close to the front end of the urine-absorption pad. As shown in FIG. 1, preferably the elastic member is not provided at least in the rear half of the section where the left side edge of the right side sheet and the right side edge of the left side sheet overlap with the overlap sheet provided in the gluteal region. If the elastic member 11 is provided in the section overlapping with the overlap sheet, then wrinkles can potentially form in the overlap sheet. From the viewpoint of preventing formation of wrinkles in the overlap sheet, the elastic member 11 provided on the left side edge of the right side sheet and the right side edge of the left side sheet is preferably provided only on the section where the overlap sheet is not provided. This will prevent formation of wrinkles in the overlap sheet and avoid skin trouble.

The stretch factor when the elastic member 11 is attached to the side sheet is preferably designed in a balanced manner so that the overlap sheet is not excessively pulled and leakage is not increased. For example, the stretch factor is preferably 1.3 to 3.0. That is, the elastic member is preferably attached to the side sheet while stretched to a factor of 1.3 to 3.0 times its natural length. More preferably, the stretch factor is 1.5 to 2.5 and even more preferably 1.7 to 2.3.

For the first embodiment, one elastic member 11 is provided on each of the right side edge 8R of the left side sheet 8 and the left side edge 9L of the right side sheet 9, but two may be provided on each, or even three or more.

The elastic member used may be a rubber thread normally used in a disposable diaper or urine-absorption pad.

The side sheets 8, 9 are preferably formed of liquid-impermeable sheets and are not particularly restricted, and for example, they may be formed of nonwoven fabrics such as spunbond nonwoven fabrics, spunbond-meltblown-spunbond (SMS) nonwoven fabrics, air-through nonwoven fabrics or the like.

In a conventional urine-absorption pad, the rear end of the right side edge of the left side sheet and the rear end of the left side edge of the right side sheet (that is, the rear ends of the barrier cuffs) are bonded to the inner side sheet with the barrier cuffs 12 folded downward toward the center in the left-right direction. This is because if the rear end of the right side edge of the left side sheet and the rear end of the left side edge of the right side sheet are not bonded to the inner side sheet, the barrier cuffs 12 will also be able to fold down toward the outer side in the left-right direction, and when the barrier cuffs 12 fold down toward the outer side in the left-right direction the barrier cuffs will no longer be able to effectively prevent leakage.

However, in a urine-absorption pad according to the first embodiment of the invention, the rear end of the right side edge of the left side sheet and the rear end of the left side edge of the right side sheet are not bonded to the inner side sheet. In a urine-absorption pad of the invention the overlap sheet is bonded to the barrier cuffs, and therefore the barrier cuffs 12 do not fold over toward the outer side in the left-right direction even if the rear end of the right side edge of the left side sheet and the rear end of the left side edge of the right side sheet are not bonded to the inner side sheet. Consequently, in a urine-absorption pad according to the first embodiment of the invention, there is no need for the rear end of the right side edge of the left side sheet and the rear end of the left side edge of the right side sheet to be bonded to the inner side sheet. Rather, if the rear end of the right side edge of the left side sheet and the rear end of the left side edge of the right side sheet are bonded to the inner side sheet, movement of the overlap sheet in the longitudinal direction will be inhibited, and therefore it is preferred for the rear end of the right side edge of the left side sheet and the rear end of the left side edge of the right side sheet to not be bonded to the inner side sheet.

The inner side sheet 7 is provided on the body side of the absorbent body 6. The inner side sheet 7 is preferably situated so as to cover as wide a range as possible of the area of the absorbent body 6, but it does not need to cover the entire area of the absorbent body 6.

The left side edge of the inner side sheet 7 is bonded to the clothing side surface of the left side sheet, while the right side edge of the inner side sheet 7 is bonded to the clothing side surface of the right side sheet. The bonding method may be any method such as adhesive bonding, heat sealing or the like, but bonding with a hot-melt adhesive is preferred. The bonding position is near the erection origin of the barrier cuff.

The inner side sheet 7 is formed of a liquid-impermeable sheet and is not particularly restricted, and may be formed of a nonwoven fabric such as spunbond nonwoven fabric, spunbond-meltblown-spunbond (SMS) nonwoven fabric, air-through nonwoven fabric or the like.

The outer side sheet 5 is not particularly restricted, and may be formed of a nonwoven fabric such as a spunbond nonwoven fabric, spunbond-meltblown-spunbond (SMS) nonwoven fabric, air-through nonwoven fabric or the like. When a leak-preventing film 10 is provided between the outer side sheet 5 and the absorbent body 6, the outer side sheet 5 may be either liquid-impermeable or liquid-permeable, but when a leak-preventing film 10 is not provided between the outer side sheet 5 and the absorbent body 6, the outer side sheet 5 is formed of a liquid-impermeable sheet.

The leak-preventing film 10 is not restricted so long as it is a liquid-impermeable film, and for example, it may be formed of a liquid-impermeable plastic film. From the viewpoint of preventing mustiness, the leak-preventing film 10 is preferably moisture-permeable.

The region in which the leak-preventing film 10 is disposed is over the entire surface of the outer side sheet 5 in the first embodiment, but it is not essential for the leak-preventing film 10 to be disposed over the entire surface of the outer side sheet 5, and the leak-preventing film 10 may be disposed only on a portion of the outer side sheet 5. However, the leak-preventing film 10 is preferably disposed at least in the region in which the absorbent body is disposed.

The absorbent body 6 is not restricted so long as it absorbs urine, and for example, it may be a liquid-absorbing core material formed by compacting a mixture of fluff pulp and super-absorbent polymer particles or the like, covered with a fluid diffusibility sheet such as a tissue.

The absorbent body 6 is distributed at least in the crotch region 3, extending in the longitudinal direction toward the abdominal region 2 and the gluteal region 4. In the crotch region 3, the absorbent body 6 has a small dimension in the left-right direction, with a narrowing shape toward the center in the left-right direction.

A second embodiment of the urine-absorption pad of the invention will now be described.

Figure 4:
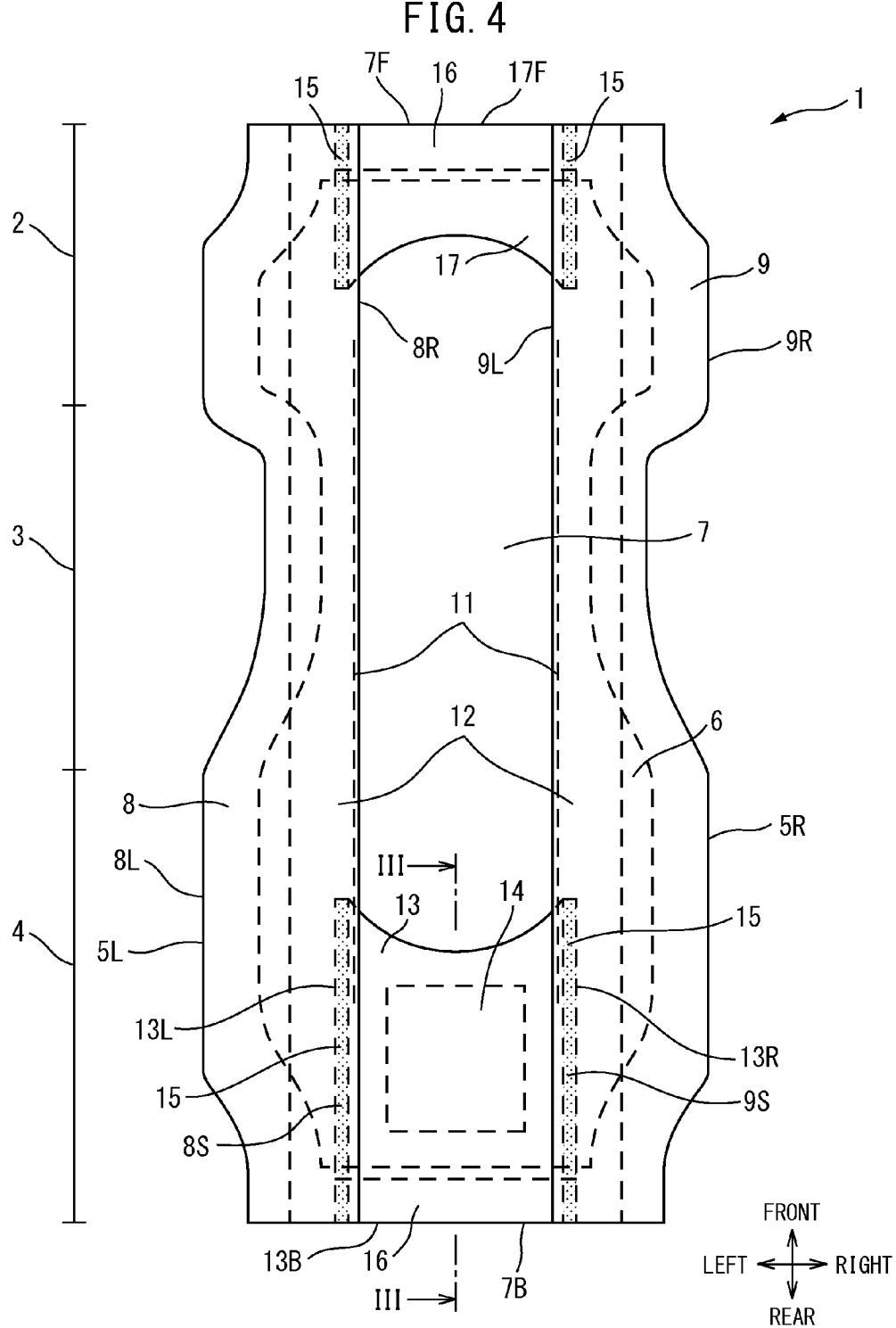
FIG. 4 is a plan view of a disposable urine-absorption pad with a bedsore-inhibition function according to a second embodiment of the invention.
Figure 5:
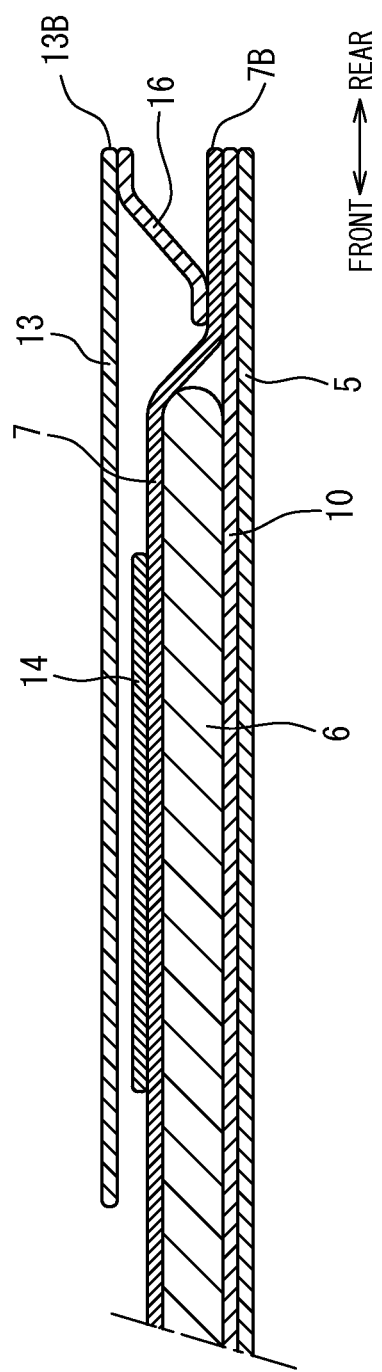
FIG. 5 is a cross-sectional view along line III-III of FIG. 4.

FIG. 4 is a plan view of a urine-absorption pad according to the second embodiment, and FIG. 5 is a cross-sectional view along line III-III of FIG. 4. The second embodiment differs from the first embodiment in that the overlap sheet 13 is bonded to the inner side sheet 7 via the tacky section 16, and in that the second overlap sheet 17 is provided in the abdominal region 2. For structural parts that are similar to those of first embodiment, the same symbols will be used as for the first embodiment and they will not be described in detail.

Figure 6:
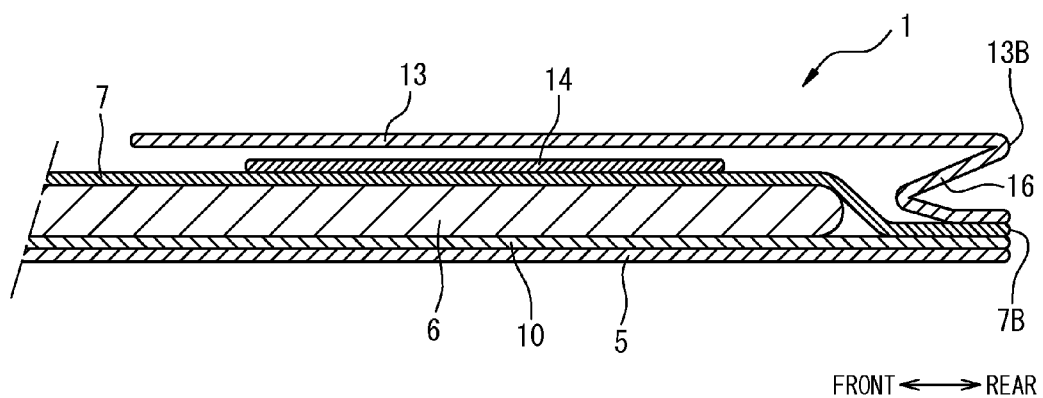
FIG. 6 is a cross-sectional view showing another example of the tacky section.

FIG. 5 is a cross-sectional view along line III-III of FIG. 4. The rear end edge 13B of the overlap sheet matches the rear end edge 7B of the inner side sheet, the rear end edge 13B of the overlap sheet being bonded to the inner side sheet 7 via a tacky section 16. The tacky section 16 shown in FIG. 5 is formed of a separate member from the overlap sheet. As shown in FIG. 6, the tacky section 16 may be formed by folding over the overlap sheet. Bonding between the tacky section 16 and the inner side sheet 7 may be accomplished by any method such as adhesive bonding, heat sealing or the like, but bonding with a hot-melt adhesive is preferred. By providing a tacky section 16, it is possible to prevent leakage of excreta such as urine to the rear end, without inhibiting movement of the overlap sheet in the longitudinal direction. Furthermore, the tacky section 16 of a separate member from the overlap sheet has the advantage of allowing independent selection of the materials for the overlap sheet and the tacky section. For example, if the overlap sheet is formed of a hydrophilic material and the tacky section is formed of a hydrophobic material, urine on the overlap sheet can also be absorbed, and leakage out of the hydrophobic tacky section can be prevented.

According to the second embodiment, a second overlap sheet 17 is provided in the abdominal region 2. The front end edge 17F of the second overlap sheet matches the front end edge 7F of the inner side sheet, the front end edge 17F of the second overlap sheet being bonded to the inner side sheet 7 through the tacky section 16. The second overlap sheet 17 having the tacky section 16 serves to prevent excreta such as urine from leaking out to the upper abdominal region side.

According to the second embodiment, the front end edge of the overlap sheet provided in the gluteal region (hereunder, the simple term "overlap sheet" will refer to the overlap sheet provided in the gluteal region) has a shape that is indented toward the rear. By having such a shape, feces will attach less easily onto the overlap sheet. The rear end edge of the second overlap sheet has a shape that is indented toward the front.

Figure 7:
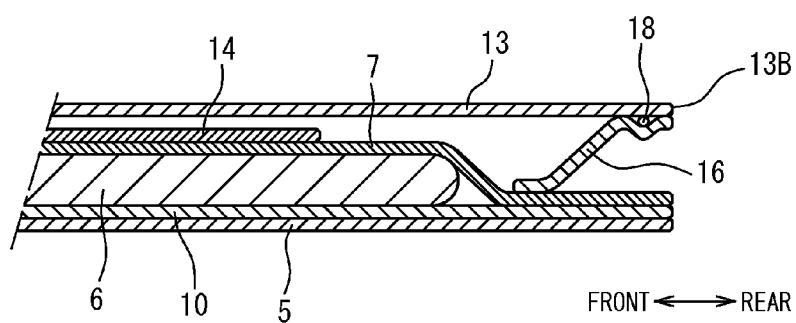
FIG. 7 is a cross-sectional view showing an embodiment in which an elastic member is provided on the rear end edge of the overlap sheet.
Figure 8:
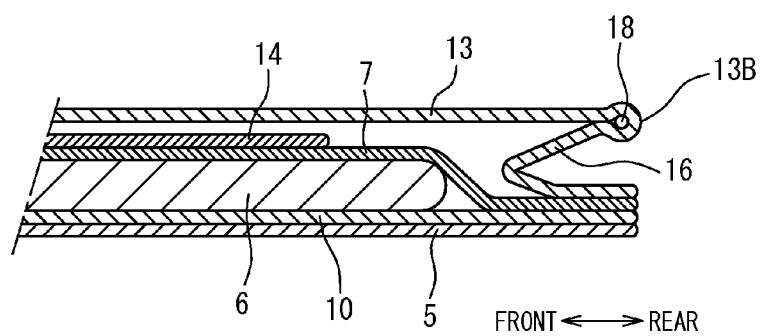
FIG. 8 is a cross-sectional view showing another embodiment in which an elastic member is provided on the rear end edge of the overlap sheet.

As shown in FIG. 7 and FIG. 8, an elastic member 18 is provided on the rear end edge 13B of the overlap sheet 13. Providing the elastic member 18 forms a pocket, helping to more effectively prevent leakage of excreta from the rear side. An elastic member may be also be provided at the front end edge 17F of the second overlap sheet 17.

Figure 11:
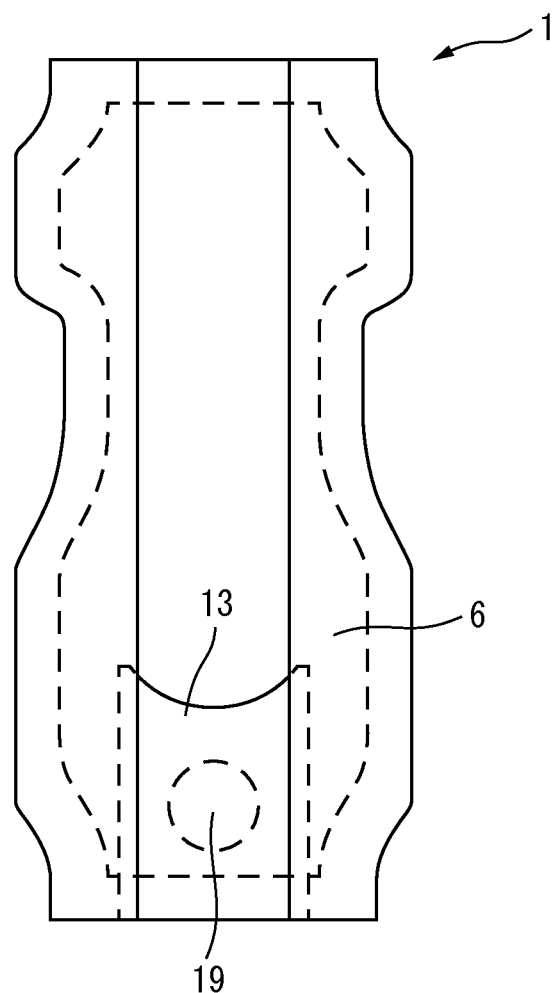
FIG. 11 is a diagram showing an example of a region without the absorbent body or a region where the absorbent body has a relatively low basis weight.

As shown in FIG. 11, a region without the absorbent body or a region where the absorbent body has a relatively low basis weight 19 may also be provided in the region where the overlap sheet 13 is provided. The shape of the region without the absorbent body or the region where the absorbent body has a relatively low basis weight 19 is not particularly restricted and may be any shape such as circular, elliptical, square, rectangular, rhomboid, hexagonal or octagonal.

Figure 12:
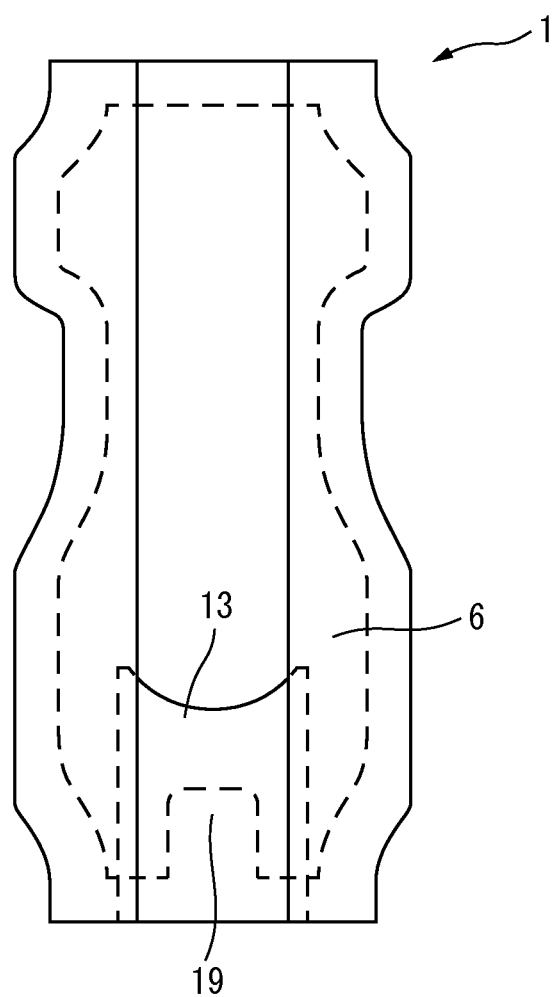
FIG. 12 is a diagram showing another example of a region without the absorbent body or a region where the absorbent body has a relatively low basis weight.

Also, as shown in FIG. 12, a region without the absorbent body may be formed by creating a notch within the shape of the absorbent body. The region without the absorbent body or the region where the absorbent body has a relatively low basis weight 19 is preferably provided at a location contacting the sacrum of the wearer when the urine-absorption pad is worn. By such reduction, including body pressure, it is possible to further reduce occurrence or aggravation of bedsores.

The urine-absorption pad of the invention can be produced in the following manner.

First, a leak-preventing film is attached to an outer side sheet, an absorbent body is placed on the leak-preventing film, an inner side sheet is layered over the absorbent body and a low friction member is attached onto the top of the inner side sheet, to fabricate a layered body comprising the outer side sheet, leak-preventing film, absorbent body, inner side sheet and low friction member. Separately, an elastic member is situated on a sheet which is to form the left side sheet and right side sheet, the left side sheet and right side sheet are fabricated, and an overlap sheet is bonded straddling the fabricated left side sheet and right side sheet to produce an assembly of the side sheets and overlap sheet. The assembly of the side sheets and overlap sheet is stacked onto the low friction member side of the layered body comprising the outer side sheet, leak-preventing film, absorbent body, inner side sheet and low friction member, and these are bonded to obtain a urine-absorption pad.

The overlap sheet of the urine-absorption pad of the invention moves easily in the longitudinal direction relative to the inner side sheet. In the case of bedridden elderly, when the bed is elevated to raise the upper body, the gluteal region is shifted forward by the weight of the body, and even for an elderly person using a wheelchair, the gluteal region is gradually shifted forward by the weight of the body during use of the wheelchair, and this can lead to occurrence or aggravation of bedsores. Since the overlap sheet of the urine-absorption pad of the invention moves easily in the longitudinal direction relative to the inner side sheet, when the gluteal region shifts forward, even if the urine-absorption pad main body does not move, the overlap sheet and inner side sheet easily slip and the overlap sheet moves together with the gluteal region, thereby allowing creation and aggravation of bedsores to be prevented.

INDUSTRIAL APPLICABILITY

The disposable urine-absorption pad with a bedsore-inhibition function of the invention, employed with a tape-type or pants-type diaper cover, can be utilized as a disposable diaper. It is particularly suitable for use as a disposable urine-absorption pad for persons prone to bedsores, such as bedridden elderly.

EXPLANATION OF SYMBOLS

1 Disposable urine-absorption pad with bedsore-inhibition function
2 Abdominal region
3 Crotch region
4 Gluteal region
5 Outer side sheet
6 Absorbent body
7 Inner side sheet
8 Left side sheet
9 Right side sheet
10 Leak-preventing film
11 Elastic member
12 Barrier cuff
13 Overlap sheet
14 Low friction member
15 Bonding region between overlap sheet and side sheet
16 Tacky section
17 Second overlap sheet
18 Elastic member
19 Region without absorbent body or region where absorbent body has relatively low basis weight
20 Hole

The invention claimed is:

1. A disposable urine-absorption pad with a bedsore-inhibition function, having front and rear and left and right ends, a body side and clothing side, and an abdominal region, crotch region and gluteal region in that order from front to rear,
   wherein the pad includes an outer side sheet, an absorbent body provided on the body side of the outer side sheet, an inner side sheet provided on the body side of the absorbent body, a left side sheet provided on the left side section of the pad and a right side sheet provided on the right side section of the pad,
   the left side edge of the left side sheet matching the left side edge of the outer side sheet, and the left side sheet and the outer side sheet being bonded along the left side edge, and the right side edge of the right side sheet matching the right side edge of the outer side sheet, and the right side sheet and the outer side sheet being bonded along the right side edge,
   the right side edge of the left side sheet and the left side edge of the right side sheet being straight linear and located more toward the body side than the inner side sheet, and forming free ends without being bonded to the inner side sheet, and an elastic member being provided on at least a portion of the right side edge of the left side sheet and at least a portion of the left side edge of the right side sheet, so that the left side sheet and the right side sheet form barrier cuffs,
   wherein
   the pad further includes an overlap sheet and a low friction member, the overlap sheet being provided in the gluteal region, the right side edge of the overlap sheet being bonded to the left side section of the right side sheet, the left side edge of the overlap sheet being bonded to the right side section of the left side sheet, and the low friction member being provided between the overlap sheet and the inner side sheet, and
   the elastic member provided on the left side edge of the right side sheet and the right side edge of the left side sheet is provided only on sections of the right side sheet and left side sheet where the overlap sheet is not provided.

2. A disposable urine-absorption pad with a bedsore-inhibition function according to claim 1, wherein the rear end of the right side edge of the left side sheet and the rear end of the left side edge of the right side sheet are not bonded to the inner side sheet.

3. A disposable urine-absorption pad with a bedsore-inhibition function according to claim 1, wherein the rear end edge of the overlap sheet matches the rear end edge of the inner side sheet, the rear end edge of the overlap sheet being bonded to the inner side sheet via a tacky section.

4. A disposable urine-absorption pad with a bedsore-inhibition function according to claim 3, wherein the tacky section is formed of a different member than the overlap sheet.

5. A disposable urine-absorption pad with a bedsore-inhibition function according to claim 3, wherein the tacky section is formed by folding over the overlap sheet.

6. A disposable urine-absorption pad with a bedsore-inhibition function according to claim 1, wherein the overlap sheet is formed of a sheet that can expand and contract in at least one direction.

7. A disposable urine-absorption pad with a bedsore-inhibition function according to claim 6, wherein the overlap sheet is disposed so that the direction in which the overlap sheet can expand and contract matches the front-rear direction of the pad.

8. A disposable urine-absorption pad with a bedsore-inhibition function according to claim 1, wherein the overlap sheet is bonded to a clothing side surface of the inner side sheet.

9. A disposable urine-absorption pad with a bedsore-inhibition function according to claim 1, wherein the overlap sheet is also provided in the abdominal region.

10. A disposable urine-absorption pad with a bedsore-inhibition function according to claim 1, wherein the front end edge of the overlap sheet provided in the gluteal region has a shape that is indented toward the rear.

11. A disposable urine-absorption pad with a bedsore-inhibition function according to claim 1, wherein the rear end edge of the overlap sheet provided in the abdominal region has a shape that is indented toward the front.

12. A disposable urine-absorption pad with a bedsore-inhibition function according to claim 1, wherein the low friction member is provided on the body side surface of the inner side sheet, and in the region contacting with the overlap sheet.

13. A disposable urine-absorption pad with a bedsore-inhibition function according to claim 1, wherein the low friction member is provided on the clothing side surface of the overlap sheet, and in the region contacting with the inner side sheet.

14. A disposable urine-absorption pad with a bedsore-inhibition function according to claim 1, wherein the elastic member is provided on the rear end edge of the overlap sheet.

15. A disposable urine-absorption pad with a bedsore-inhibition function according to claim 1, wherein the low friction member is composed of a low friction sheet with holes.

16. A disposable urine-absorption pad with a bedsore-inhibition function according to claim 1, wherein a plurality of low friction members are disposed at spacings.

17. A disposable urine-absorption pad with a bedsore-inhibition function according to claim 1, wherein the region where the overlap sheet is provided has a region without the absorbent body or a region where the absorbent body has a relatively low basis weight.

18. A disposable urine-absorption pad with a bedsore-inhibition function according to claim 1, wherein the overlap sheet is a hydrophilic sheet.

* * * * *